United States Patent [19]

Kida et al.

[11] 4,032,325

[45] June 28, 1977

[54] METHOD FOR CONTROLLING WEEDS WITH AMINO ACID HIGHER ALKYL ESTERS

[75] Inventors: Takao Kida, Yokosuka; Hiroshi Mizuno, Yokohama; Masaru Okutsu, Kawasaki, all of Japan

[73] Assignee: Ajinomoto Co., Inc., Tokyo, Japan

[22] Filed: Oct. 15, 1974

[21] Appl. No.: 514,745

[30] Foreign Application Priority Data

Oct. 19, 1973 Japan .......................... 48-118316
Feb. 14, 1974 Japan ............................ 49-18050

[52] U.S. Cl. .................................. 71/95; 71/103; 71/106; 71/111; 71/123
[51] Int. Cl.² .................... A01N 9/22; A01N 9/14; A01N 9/24
[58] Field of Search ...................... 71/106, 95, 103

[56] References Cited

UNITED STATES PATENTS

| | | |
|---|---|---|
| 2,290,174 | 7/1942 | Epstein et al. ..................... 424/311 |
| 2,888,383 | 5/1959 | Byrne ................................ 424/54 |
| 2,965,534 | 12/1960 | Darlington ......................... 424/311 |
| 2,965,636 | 12/1960 | Moore et al. ..................... 71/106 X |
| 3,619,168 | 11/1971 | Mecklenborg et al. ............. 71/106 |
| 3,712,804 | 1/1973 | Muller et al. ..................... 71/106 X |
| 3,736,112 | 5/1973 | Abramitis et al. ............... 71/106 X |
| 3,758,525 | 9/1973 | Yoshida et al. ................ 424/319 X |

FOREIGN PATENTS OR APPLICATIONS 2,203,228 9/1972 Germany .......................... 424/311

*Primary Examiner*—Joseph Paul Brust
*Attorney, Agent, or Firm*—Sherman & Shalloway

[57] ABSTRACT

A herbicidal composition comprising a herbicidal amount of an active compound selected from the group consisting of acid addition salts of higher alkyl esters of amino acids, acid addition salts of N-lower alkyl substitution products of said esters and quaternary ammonium salts of N-lower alkyl substitution products of said esters, and a diluent or carrier, and a method for controlling weeds using said herbicidal composition.

6 Claims, No Drawings

METHOD FOR CONTROLLING WEEDS WITH AMINO ACID HIGHER ALKYL ESTERS

This invention relates to a herbicidal composition of an amino acid higher alkyl ester type which has an excellent weed controlling effect, especially a germination inhibitory activity and a herbicidal activity, and which exhibits a markedly reduced toxicity on man, poultry, domestic animals, fish and oher non-mammalian aquatic animals and also a reduced residual toxicity in soil; and to a method for controlling weeds.

The herbicidal composition of this invention is useful for controlling weeds growing in various loci such as fields, paddies, orchards, forests and gardens, but can be applied especially preferably to post-emergence weed control for agriculture and horticulture in fields, paddies and orchards, especially for controlling weeds in paddies.

Active compounds of the carbamate, acid amide, diphenylether, s-triazine, urea and dipyridyl types have previously been used as herbicides against weeds in fields and paddies, but these conventional herbicides have not been entirely satisfactory in respect of residual toxicity in soil and toxicity on man, poultry, domestic animals, fish and other non-mammalian aquatic animals. Thus, their use has been limited because of the need to control pollution.

The inventors of the present application have been engaged in the development of herbicides which exhibit an excellent herbicidal effect without posing any such pollution problem. As a result, they found that an active compound selected from the group consisting of acid addition salts of higher alkyl esters of amino acids, preferably those in which the alkyl group contains 8 to 22 carbon atoms, acid addition salts of N-lower alkyl substitution products of said alkyl esters, preferably those in which the lower alkyl group contains 1 to 4 carbon atoms, and quaternary ammonium salts of N-lower alkyl substitution products of said alkyl esters exhibits an excellent germination inhibitory activity and a herbicidal activity on broadleaf weeds in the paddy field such as barnyard-grass (*Echinochloa oryzicola* VASING), *Monachoria vaginalis* PRESL, *Eleocharis acicularis* ROEM et SHULT, and *Cyperus difformis* L. and upland weeds such as *Digifaria adscendens* HENR, or *Amaranthus viridis* L. without causing such a pollution problem. It has also been found that the above active compounds exhibit an outstanding effect within a very short period of time, for example, within 2 to 3 days, against broadleaf weeds in paddy fields, the effect being not reduced even in a flooded paddy field, and has no phytotoxicity on rice plants, and further that the compound exhibits an excellent herbicidal acitivty on the above upland weeds without phytotoxicity on plants cultivated in upland.

It is therefore an object of this invention to provide a herbicidal composition of an amino acid higher alkyl ester type herbicidal composition having an excellent herbicidal effect and causing no pollution problem with its markedly reduced toxicity on man, domestic animals, poultry, fish and other non-mammalian aquatic animals and also a markedly reduced residual toxicity in soil; and a method for weed control using this composition.

The active compound in the herbicidal composition of this invention is selected from the group consisting of acid addition salts of higher alkyl esters, preferably $C_{8-22}$ higher alkyl esters, of amino acids, acid addition salts of N-lower alkyl substitution products, preferably $C_{1-4}$ lower alkyl substitution products, of said esters, and quaternary ammonium salts of N-lower alkyl substitution products of said esters. Preferred active compounds are, for example, those of the following formulae (1) and (2).

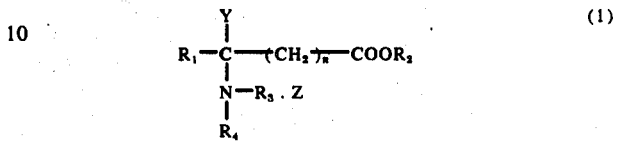

(1)

wherein $R_1$ is a member selected from the group consisting of a hydrogen atom, alkyl groups containing 1 to 4 carbon atoms,

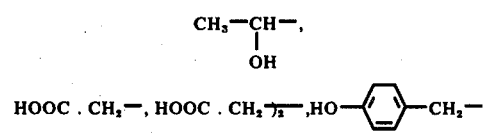

and $H_2N.(CH_2)_4$; $R_2$ is an alkyl group containing 8 to 22 carbon atoms; Y is a hydrogen atom or methyl group; $R_3$ and $R_4$ are each a member of the group consisting of a hydrogen atom and a methyl group; Z is an inorganic or organic acid group; and $n$ is 0 or an integer of 1 to 5, and when $n$ is an integer of 1 to 5, both of $R_1$ and Y are hydrogen atoms;

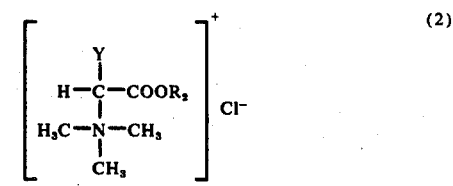

(2)

wherein Y and $R_2$ are the same as defined with respect to formula (1).

Various amino acids such as α-amino acid, β-amino acid, and ω-amino acid can be utilized as the amino acid component of the compounds of formula (1) and (2) above. Examples of preferred amino acids are glycine, alanine, β-alanine, valine, norvaline, leucine, isoleucine, norleucine, tyrosine, threonine, 2-aminoisobutyric acid, 6-aminocaproic acid, lysine, and arginine, and N—$C_{1-4}$ alkyl substitution products, such as N-methyl or N-ethyl substitution products, of these, such as glycine betaine, N,N'-dimethylvaline, and N,N'-dimethylalanine. The amino acids may be optically active ones or racemic modifications.

Examples of the ester portion of the above preferred compounds of formulae (1) and (2) are esters of straight chain or branched alkyls containing 8 to 22 carbon atoms such as octyl, decyl, lauryl, myristyl, cetyl, stearyl, 2-hexyldecyl and 2-octyldecyl esters. Of these, the decyl and lauryl esters are preferred.

Both organic acids and inorganic acids can be utilized as the acid group Z which forms an acid addition salt in the formula (1). Examples of preferred acids are hydrochloric acid, acetic acid, p-toluenesulfonic acid, oxalic acid, and pyroglutamic acid.

The solubility of the active component used in this invention differs according to the type of the acid addition salt, the number of carbon atoms of the alkyl esters, etc., but generally, it is water-soluble. Where the solubility of the active ingredient is very low, it is preferred to utilize a suitable dispersing agent.

The active ingredient used in this invention can be used conjointly with other known herbicides or fungicides. The conjoint use of it with a known herbicide, 3,3'-dimethyl-4-methoxybenzophenone has been found to exhibit a unique synergistic effect. The 3,3'-dimethyl-4-methoxybenzophenone has an excellent herbicidal effect when applied in the pre-emergence stage, but does not show a satisfactory herbicidal effect when applied in the post-emergence stage. When this 3,3'-dimethyl-4-methoxybenzophenone is used in admixture with the active ingredient used in the present invention, the mixture shows an excellent synergistic herbicidal effect in post-emergence application. It may be recommended that the active compound (A) of this invention and the 3,3'-dimethyl-4-methoxybenzophenone (B) are used in an (A) : (B) weight ratio of 2 : 8 to 8 : 2, more preferably 4 : 6 to 6 : 4.

The herbicidal composition of this invention can be formulated in any desired formulation such as dust, granule, pellet, wettable powder, emulsifiable concentrate or dispersed liquid using various solid and liquid diluent or carriers known in the art. Examples of solid diluents or carriers are clay, white carbon, bentonite, kaolin, diatomaceous earth, starch, and gum arabic, with or without a dispersing agent or emulsifier. Examples of liquid diluents or carriers are water, water containing a dispersing agent or emulsifier, dioxane, isophorone or ethanol. The above-mentioned dispersing agent or emulsifier may, for example, be soap, sulfuric acid esters of higher alcohols, alkylsulfonate salts, quaternary ammonium salts, polyalkylene oxides, polyoxyalkylene ethers, or alkali metals or calcium salts of ligninsulfonic acid.

The amount of the above diluent or carrier to be used in the composition of this invention can be suitably selected, and for example, the content of the active compound (including a mixture of the active compounds) can be about 1 to about 99% by weight based on the weight of the herbicidal composition. The amount of the active compound can be suitably selected also according to the type of formulation. For example, the amount may be about 10 to about 90% by weight in the case of emulsifiable concentrate, suspension or wettable powder, and it may be frequently about 10 to about 30% by weight when the formulation is granule or pellet.

According to this invention, there can be provided a method for controlling weeds, which comprises applying to weeds or the locus where weeds are growing or will grow a herbicidal amount of an active compound selected from the group consisting of acid addition salts of higher alkyl esters of amino acids, acid addition salts of N-lower alkyl substitution products of said esters and quaternary ammonium salts of N-lower alkyl substitution products of said esters. The active compound can be applied as a mixture of it with a known herbicide, 3,3'-dimethyl-4-methoxybenzophenone.

The application of the herbicidal composition of this invention is preferably done in the post-emergence stage. For example, the composition is applied to weeds in paddies desirably in the early stage of germination. As will be shown later in the Examples, the herbicidal composition of this invention exhibits an excellent herbicidal effect without causing phytotoxicity even when applied to the period of growth of weeds after rice plant seedlings have been transplanted in paddies. In order to control upland weeds, a foliar treatment of weeds with the herbicidal composition of this invention gives good results.

The rate of application of the active ingredients can be suitably varied according to the time of application, the type of weeds, the type of the active compound, and the type of formulation. Generally, the rate of the herbicidal composition to be applied is about 50 to about 100 g per are. Often, amounts of about 100 to about 400 g per are are employed in the case of upland weeds, and about 50 to about 150 g per are in the case of weeds in paddies. When a mixture of the active compound and 3,3'-dimethyl-4-methoxybenzophenone is used, the preferred amount of the mixture is about 30 to about 60 g per are.

Examples of the herbicide of this invention are shown below. All parts in the Examples are by weight.

EXAMPLE 1

Glycine lauryl ester DL-pyroglutamate (20 parts), 2 parts of white carbon, 2 parts of sodium ligninsulfonate, 4 parts of a polyoxyethylene alkyl ether and 72 parts of clay were mixed and pulverized to form 100 parts of a wettable powder.

EXAMPLE 2

DL-valine lauryl ester hydrochloride (10 parts), 15 parts of starch, 72 parts of bentonite and 3 parts of a sodium salt of lauryl alcohol sulfate ester were mixed and pulverized to form 100 parts of granules.

EXAMPLE 3

Betaine lauryl ester hydrochloride (50 parts), 10 parts of an emulsifier (SORPOL, a registered tradename for a product of Toho Chemical Co., Ltd., Japan) and 40 parts of water were mixed to form 100 parts of an emulsifiable concentrate.

The control effect of the herbicide of this invention against weeds in paddies and upland weeds will be described below.

EXAMPLE 4

Treatment of irrigated soil:

Soil from a rice paddy field was filled in synthetic resin pots each having an inside diameter of 8 cm, and seeds of rice plant (Nihonbare variety), barnyard grass (*Echinochloa oryzicola* VASING), *Monochoria vaginalis* PRESL., and other broad-leaf weeds were sown. Then, the pots were irrigated so that the depth of water became 3 cm. Then, at the stage where the first leaves sprouted (in the case of barnyard grass) and at the stage of growth (the other weeds), these weeds were treated with an aqueous solution of the active ingredient in the amount indicated in Table 1 (those not soluble in water were first dissolved in dioxane and then in water). Ten days after the treatment, the treated pots were examined for a herbicidal effect and the state of growth of the weeds. The results are shown in Table 1 according to the following scale of evaluation.

Table 1

| Compound No. | Rate (Active ingredient) g/a | Herbicidal Effect Echinochloa oryzicola VASING | Monachoria vaginalis PRESL | Broadleaf weed | Cyperus difformis L. |
|---|---|---|---|---|---|
| 1* | 100 | 3 | 2 | 4 | 4 |
| 2 | 100 | 3 | 2 | 4 | 4 |
|   | 50 | 3 | 2 | 4 | 3 |
| 3 | 100 | 4 | 2 | 4 | 2 |
|   | 50 | 3 | 2 | 4 | 2 |
| 4 | 100 | 4 | 4 | 4 | 4 |
|   | 50 | 4 | 4 | 4 | 4 |
|   | 25 | 3 | 3 | 3 | 3 |
| 5 | 100 | 4 | 2 | 4 | 3 |
| 6 | 100 | 3 | 1 | 3 | 3 |
| 7* | 100 | 3 | 2 | 3 | 3 |
| 8 | 100 | 4 | 2 | 4 | 3 |
| 9 | 100 | 4 | 4 | 4 | 4 |
|   | 50 | 4 | 4 | 4 | 4 |
|   | 25 | 3 | 3 | 3 | 3 |
| 10 | 100 | 3 | 1 | 2 | 2 |
| 11 | 100 | 2 | 2 | 1 | 2 |
| 12 | 100 | 2 | 2 | 2 | 2 |
| 13 | 100 | 2 | 2 | 2 | 2 |
| 14 | 100 | 2 | 2 | 2 | 2 |
| 15 | 100 | 2 | 3 | 3 | 2 |
| 16 | 100 | 2 | 2 | 2 | 2 |

Note
1* N,N-dimethyl-DL-valinelauryl ester oxalate
2 Glycine lauryl ester DL-pyroglutamate
3 DL-alaninelauryl ester hydrochloride
4 DL-valinelauryl ester hydrochloride
5 DL-leucinelauryl ester hydrochloride
6 Glycinedecyl ester hydrochloride
7* DL-tyrosine lauryl ester hydrochloride
8 DL-threoninedecyl ester hydrochloride
9 2-aminoisobutyric acid lauryl ester hydrochloride
10 DL-lysine lauryl ester hydrochloride
11 Betaine lauryl ester hydrochloride
12 DL-aspartic acid lauryl ester hydrochloride
13 DL-glutamic acid lauryl ester hydrochloride
14 DL-tyrosine lauryl ester hydrochloride
15 DL-alanine lauryl ester oxalate
16 ε-Aminocaproic acid lauryl ester DL-pyroglutamate
[*insoluble in water (dissolved in water after having been dissolved in dioxane)]

Herbicidal effect:
0: none
1: slight
2: ordinary
3: strong
4: the weeds were withered

EXAMPLE 5

Herbicidal effect on various weeds in paddies:
The following plants (unless otherwise specified, they were all in the 5-leaf stage) were transplanted in synthetic resin pots each having an inside diameter of 12 cm. The pots were irrigated to a water depth of 4 cm. After these plants rooted (7 days later), they were treated with a chemical liquid containing a predetermined amount of the active ingredient dissolved therein. The plants were examined 6 days after the treatment. The standard of evaluation was the same as in Example 4.

Table 2

(Weeding spectrum)

| Weeds | Compound No. | 2 | 3 | 4 | 4 | 5 | 9 | 9 |
|---|---|---|---|---|---|---|---|---|
| g/a |  | 200 | 200 | 200 | 100 | 200 | 200 | 100 |
| Lobelia chinensis LOUR |  | 4 | 4 | 4 | 4 | 4 | 4 | 4 |
| Lindernia procumbens PHILCOX |  | 4 | 4 | 4 | 4 | 4 | 4 | 4 |
| Vandellia angustifolia BENTH |  | 3 | 4 | 4 | 4 | 3 | 4 | 4 |
| Dopatrium junceum HAMILT |  | 3 | 4 | 4 | 4 | 3 | 4 | 4 |
| Ludwigia prostrata ROXB. |  | 4 | 4 | 4 | 4 | 4 | 4 | 4 |
| Rotala indica KOEHNE |  | 4 | 4 | 4 | 4 | 4 | 4 | 4 |
| Elatine triandra SCHK |  | 4 | 4 | 4 | 4 | 4 | 4 | 4 |
| Callitriche Verna L. |  | 4 | 4 | 4 | 4 | 4 | 4 | 4 |
| Monochoria vaginalis PRESL. |  | 3 | 4 | 4 | 4 | 3 | 4 | 4 |
| Aneilema Keisak HASSK. |  | 2 | 2 | 2 | 2 | 2 | 2 | 2 |
| Echinochloa Oryzicola VASING |  | 4 | 4 | 4 | 4 | 4 | 4 | 4 |
| Spirodela polyrhiza SCHLEID. |  | 4 | 4 | 4 | 4 | 4 | 4 | 4 |
| Lemna paucicostata HEGELM |  | 4 | 4 | 4 | 4 | 4 | 4 | 4 |
| Potamogeton distinctus A. BENN. |  | 3 | 3 | 3 | 3 | 3 | 3 | 3 |
| Cyperus difformis L |  | 4 | 4 | 4 | 4 | 4 | 4 | 4 |
| Eleocharis acicularis ROME et SCHULT |  | 3 | 3 | 4 | 3 |  | 4 | 3 |

Note:
The compound numbers are the same as those described in the footnote to Table 1.

EXAMPLE 6

Herbicidal activity in an overflooded condition:
A chain link was placed in the lower layer of Wagner pots (1/5000 are), and pebbles and sand were successively packed onto it. Soil of a rice paddy was filled in the pots as an upper layer. A cock was fixed to the discharge opening at the bottom of the pot so that water at a desired flow rate could be discharged from the pot. Seeds of barnyard grass (*Echinochloa oryzicola* VASHING), *Monochoria vaginalis* PRESL., and other broadleaved weeds were sown, and at the same time, rice plant seedlings (Nihonbare variety) were transplanted in the pots. At the beginning of growing of weeds (3 days after the transplantation) and at the stage of growth of the weeds (8 to 10 days after the transplantation), a chemical liquid containing a predetermined amount of the active ingredient dissolved therein was applied to the weeds. For 3 days after the treatment, the water was overflooded at a rate of 2 cm/day, and thereafter, the weeds were allowed to grow in an irrigated condition with a water depth of 3 cm. On the 24th day after the transplantation, the remaining weeds were pulled up, and their dry weight was measured. The weight was compared with that in a non-treated lot, and the rate of control was calculated according to the following equation, and the results are shown in Table 3.

$$\text{Rate of control} = \left(1 - \frac{\text{Dry weight of weeds in the treated lot}}{\text{Dry weight of weeds in the non-treated lot}}\right) \times 100 \text{ (\%)}$$

Table 3

| Compound No. | Treating conditions* | Flooded water | Rate of control (%) Echinochloa oryzicola VAS-ING | Monachoria vaginalis PRESL | Broad leaf weed | Cyperus difformis L | Phytotoxicity |
|---|---|---|---|---|---|---|---|
| 4 | +3, 100g/a | − | 90 | 100 | 100 | 60 | − |
|   | +3, 100g/a | + | 80 | 100 | 100 | 90 | − |
|   | +3, 50g/a | − | 50 | 90 | 90 | 60 | − |
|   | +3, 50g/a | + | 80 | 100 | 100 | 60 | − |
|   | +3, 25g/a | − | 30 | 100 | 80 | 80 | − |
|   | +3, 25g/a | + | 90 | 100 | 90 | 60 | − |
|   | +10, 100g/a | − | 20 | 70 | 100 | 30 | − |
|   | +10, 100g/a | + | 80 | 100 | 100 | 80 | − |
|   | +10, 50g/a | − | 10 | 70 | 80 | 10 | − |
|   | +10, 50g/a | + | 80 | 90 | 90 | 60 | − |
|   | +3, 50g/a | − | 90 | 100 | 100 | 80 | − |
|   | +10, 50g/a | + | 80 | 100 | 100 | 80 | − |
| 9 | +3, 100g/a | − | 100 | 100 | 90 | 50 | − |
|   | +3, 100g/a | + | 100 | 90 | 100 | 80 | − |
|   | +3, 50g/a | − | 100 | 90 | 90 | 70 | − |
|   | +3, 50g/a | + | 100 | 90 | 90 | 30 | − |
|   | +8, 100g/a | − | 100 | 90 | 100 | 90 | − |
|   | +8, 100g/a | + | 100 | 90 | 100 | 90 | − |
|   | +8, 50g/a | − | 30 | 80 | 100 | 80 | − |
|   | +8, 50g/a | + | 100 | 90 | 100 | 80 | − |

Note:
The compound numbers were the same as those in Table 1.
* +3, +8 and +10 respectively mean that the treatment was performed on the 3rd, 8th and 10th day after the transplatation.

As demonstrated above, the active compounds in accordance with this invention exhibited a high herbicidal effect even when used in a flooded paddy field on the 3rd to the 10th day after the transplantation, and caused no phytotoxicity on rice plants.

Some examples of formulation of the mixed active ingredient will be shown below.

EXAMPLE 7

DL-valine lauryl ester hydrochloride; 25 parts
3,3′-dimethyl-4-methoxybenzophenone; 25 parts
White carbon; 2 parts
Sodium ligninsulfonate; 2 parts
Polyoxyethylene alkyl ether; 4 parts
Clay; 42 parts
The above ingredients were mixed and pulverized to form 100 parts of a wettable powder.

EXAMPLE 8

DL-valinelauryl ester hydrochloride; 7 parts
3,3′-dimethyl-4-methoxybenzophenone; 7 parts
Bentonite; 76 parts
Calcium ligninsulfonate; 10 parts
The above ingredients were mixed uniformly, and granulated to form 100 parts of granules.

Examples will further be given in order to illustrate the herbicidal effect of the mixed active ingredient against weeds in paddies.

Table 4

| Chemicals | | Amount of Chemical (act. ive ingredient (g/are) | Rate of residual weeds (%) Barnyard grass | | | Broad-leaved grass | Cyperus difformis L |
|---|---|---|---|---|---|---|---|
| | | | Before the one-leaf stage | 1 - leaf to 1.5 - leaf stage | 1.5 - to 2 - leaf stage | | |
| Single compound | No. 1 | 3.2 | 90 | 100 | 100 | 100 | 100 |
|   |   | 10 | 70 | 75 | 80 | 60 | 85 |
|   |   | 18 | 40 | 40 | 60 | 30 | 60 |
|   |   | 32 | 10 | 20 | 30 | 10 | 40 |
|   |   | 56 | 0 | 10 | 30 | 5 | 40 |
|   | No. 2 | 3.2 | 80 | 90 | 100 | 70 | 95 |
|   |   | 10 | 40 | 70 | 85 | 50 | 80 |
|   |   | 18 | 10 | 40 | 45 | 20 | 50 |
|   |   | 32 | 0 | 10 | 10 | 10 | 30 |
|   |   | 56 | 0 | 0 | 5 | 0 | 30 |
|   | No. 3 | 3.2 | 70 | 90 | 100 | 60 | 70 |
|   |   | 10 | 40 | 60 | 70 | 35 | 50 |
|   |   | 18 | 10 | 40 | 40 | 20 | 50 |
|   |   | 32 | 0 | 20 | 20 | 2 | 20 |
|   |   | 56 | 0 | 0 | 0 | 0 | 20 |
|   | No. 4 | 3.2 | 80 | 95 | 100 | 75 | 70 |
|   |   | 10 | 50 | 60 | 65 | 30 | 50 |
|   |   | 18 | 20 | 20 | 30 | 10 | 40 |
|   |   | 32 | 0 | 5 | 10 | 5 | 10 |
|   |   | 56 | 0 | 0 | 0 | 0 | 10 |
|   | DMB | 3.2 | 10 | 70 | 70 | 20 | 3 |
|   |   | 10 | 0 | 40 | 40 | 2 | 1 |
|   |   | 18 | 0 | 30 | 30 | 4 | 0 |
|   |   | 32 | 0 | 20 | 30 | 0 | 0 |
|   |   | 56 | 0 | 10 | 30 | 0 | 0 |
| Mixtures | No. 1 DMB | 18 18 | 0 | 10 | 15 | 0 | 0 |
|   | No. 2 DMB | 18 18 | 0 | 8 | 9 | 0 | 0 |
|   | No. 3 DMB | 18 10 | 0 | 8 | 15 | 0 | 0 |
|   | No. 3 DMB | 18 18 | 0 | 7 | 9 | 0 | 0 |
|   | No. 3 DMB | 18 18 | 0 | 0 | 7 | 0 | 0 |
|   | No. 4 DMB | 18 18 | 0 | 0 | 8 | 0 | 0 |

The following Example shows the control effect of the compounds of formula (2) against upland weeds.

EXAMPLE 9

Soil from fields was filled in synthetic resin pots each having an inside diameter of 8 cm, and seeds of barnyard grass, *Amaranthus viridis* L. and *Digitaria adscendens* HENR. were sown. At the 2- to 3-leaf stage, an aqueous solution of each of the effective components in a prescribed amount was sprayed on the leaves of the weeds in an amount of 10 ml. per pot using a spray gun. The state of growth was observed on the 7th day from the treatment, and the herbicidal effect was shown on the same scale as used in Example 4. The results are shown in Table 5 below.

Table 5

| Compound No. | Concentration (ppm) | Herbicidal effect | | |
|---|---|---|---|---|
| | | Barnyard grass | Amaranthus viridis L. | Digitaria adscendens HENR. |
| 1 | 1000 | 3 | 3 | 3 |
| | 2000 | 3 | 4 | 3 |
| 2 | 1000 | 3 | 3 | 3 |
| | 2000 | 4 | 4 | 4 |
| 3 | 1000 | 3 | 3 | 3 |
| | 2000 | 3 | 4 | 3 |

Note:
No. 1: Betaine decylester hydrochloride
No. 2: Betaine lauryl ester hydrochloride
No. 3: Betaine myristyl ester hydrochloride

What we claim is:

1. A method for controlling *Lobelia chinensis* LOUR, *Lindernia procumbens* PHILCOX, *Vandellia Angustifolia* BENTH, *Dopatrium junceum* HAMILT, *Ludwigia prostrata* ROXB., *Rotala indica* KOEHNE, *Elatine triandra* SCHK, *Callitriche Verna* L., *Monochoria vaginalis* PRESL., *Aneilema Keisak* HASSK., *Echinochloa Oryzicola* VASING, *Spirodela polyrhiza* SCHLEID., *Lemna paucicostata* HEGELM, *Potamogeton distinctus* A. BENN., *Cyperus difformis* L, *Eleocharis acicularis* ROME et SCHULT, *Amaranthus viridis* L., or *Digifaria adscendens* HENR. weeds, which comprises applying to said weeds, or the locus where said weeds are growing or will grow, a herbicidal amount of an active compound selected from the group consisting of acid addition products of higher alkyl esters of amino acids, acid addition salts of N-lower alkyl substitution products of said esters and quaternary ammonium salts of N-lower alkyl substitution products of said esters wherein said active compound is selected from compounds of formula (1)

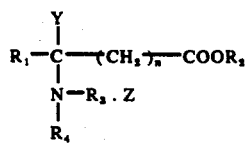

wherein $R_1$ is a member selected from the group consisting of a hydrogen atom, alkyl containing 1 to 4 carbon atoms,

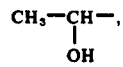

$R_2$ is alkyl containing 8 to 22 carbon atoms, Y is a hydrogen atom or methyl, each of $R_3$ and $R_4$ is a member selected from the group consisting of a hydrogen atom and lower alkyl of 1 to 4 carbon atoms, Z is an inorganic or organic acid group selected from the group consisting of hydrochloric acid, acetic acid, p-toluene sulfonic acid, oxalic acid and pyroglutamic acid, *n* is 0 or an integer of 1 to 5 and, when an integer of 1 to 5, both $R_1$ and Y are hydrogen atoms, and compounds of formula (2)

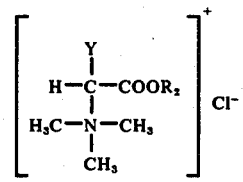

wherein Y and $R_2$ are the same as defined above.

2. The method of claim 1 wherein the rate of said active compound to be applied is 50 to 100 g per are.

3. The method of claim 1 wherein said active compound is selected from compounds of formula (1).

4. The method of claim 1 wherein said active compound is applied in the post-emergence stage.

5. The method of claim 1 wherein said active compound is selected from the group consisting of
N,N-dimethyl-DL-valinelauryl ester oxalate,
Glycine lauryl ester DL-pyroglutamate,
DL-alaninelauryl ester hydrochloride,
DL-valinelauryl ester hydrochloride,
DL-leucinelauryl ester hydrochloride,
Glycinedecyl ester hydrochloride,
DL-threoninedecyl ester hydrochloride,
2-aminoisobutyric acid lauryl ester hydrochloride,
Betaine lauryl ester hydrochloride,
DL-alanine lauryl ester oxalate,
ε-aminocaproic acid lauryl ester DL-pyroglutamate,
Betaine decyl ester hydrochloride, and
Betaine myristyl ester hydrochloride.

6. The method of claim 1 wherein each of $R_3$ and $R_4$ is a member selected from the group consisting of a hydrogen atom and methyl.

* * * * *